(12) United States Patent
Uselius et al.

(10) Patent No.: US 8,663,477 B2
(45) Date of Patent: Mar. 4, 2014

(54) CHROMATOGRAPHY COLUMN STAND

(75) Inventors: Per Uselius, Uppsala (SE); Kyril Dambuleff, Frenchtown, NJ (US); John Davis, Hucclecote (GB)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/528,973

(22) Filed: Jun. 21, 2012

(65) Prior Publication Data

US 2013/0341482 A1  Dec. 26, 2013

(51) Int. Cl.
*B01D 15/08* (2006.01)

(52) U.S. Cl.
USPC ........................................ 210/656; 210/198.2

(58) Field of Classification Search
USPC .................. 210/635, 656, 659, 198.2; 95/82; 96/101
See application file for complete search history.

(56) References Cited

U.S. PATENT DOCUMENTS

| | | | |
|---|---|---|---|
| 5,021,162 A * | 6/1991 | Sakamoto et al. | 210/635 |
| 5,667,675 A * | 9/1997 | Hatch et al. | 210/198.2 |
| 6,736,974 B1 | 5/2004 | Mann | |
| 8,066,876 B2 * | 11/2011 | Hampton et al. | 210/198.2 |
| 2006/0124525 A1 * | 6/2006 | Bellafiore | 210/198.2 |
| 2007/0138098 A1 * | 6/2007 | Spencer | 210/656 |
| 2008/0290016 A1 * | 11/2008 | Bailey et al. | 210/198.2 |
| 2008/0308498 A1 * | 12/2008 | Davis et al. | 210/656 |
| 2009/0039023 A1 * | 2/2009 | Uselius et al. | 210/656 |
| 2009/0078634 A1 * | 3/2009 | Dunkley et al. | 210/198.2 |

* cited by examiner

*Primary Examiner* — Ernest G Therkorn (57) ABSTRACT

A method for conducting maintenance on a chromatography column (1; 51), said column comprising a column tube (32), a top end cell (20) and a bottom end cell (26), where during chromatography said column tube (32) is secured between said top end cell (20) and said bottom end cell (26). Said method comprises the step of rotating at least the top end cell (20) 180 degrees around a horizontal axis before maintenance is conducted to the top end cell (20).

7 Claims, 10 Drawing Sheets

CHROMATOGRAPHY COLUMN STAND

FIELD OF THE INVENTION

The present invention relates to a stand for holding a chromatography column and to a method for conducting maintenance to a chromatography column.

BACKGROUND OF THE INVENTION

Chromatography columns are typically comprised of a column tube with a top end cell covering the top opening of the tube and a bottom end cell covering the bottom opening of the tube. A chromatography column with variable column height also comprises a plunger or adaptor integrated in the top end cell, which adaptor can be moved to different heights within the column tube. The top end cell (possibly integrated with an adaptor) and bottom end cell comprise further sample inlet/outlet, sample distribution means, filter, net, O-rings and seals. Filters, nets, distribution means, O-rings and seals may need to be replaced or cleaned after some time. A common problem during maintenance of chromatography columns is disassembly and assembly of parts. Due to the heavy parts of large chromatography columns typically a hoist is needed for separating them. However a number of hoist free maintenance solutions for chromatography columns have been described in different patents. For example in U.S. Pat. No. 6,736,974 a method of accessing the interior of a chromatography column without the use of a crane is described. A plunger is connected to a drive system which can raise the plunger above a top of the column cylinder thereby allowing intrusive maintenance.

Maintenance and replacement of different parts in the top end cell and the bottom end cell of a chromatography column is still difficult due to the heavy parts.

SUMMARY OF THE INVENTION

An object of the invention is to facilitate maintenance of chromatography columns.

A further object of the invention is to improve safety and convenience for the operator during maintenance.

This is achieved in a method for conducting maintenance on a chromatography column.

This is also achieved with a stand for holding a chromatography column.

Hereby, the top end cell could be rotated such that the filter, net and distribution means will be kept together by gravitational force which will simplify disassembly of the different parts. The different parts and fasteners are also more easily reached when the top end cell has been rotated. The top end cell does not need to be removed. The maintenance is performed without the use of a separate device and the stand itself serves as a maintenance device.

Suitable embodiments are described in the dependent claims.

DETAILED DESCRIPTION OF THE INVENTION

Figure 1A:
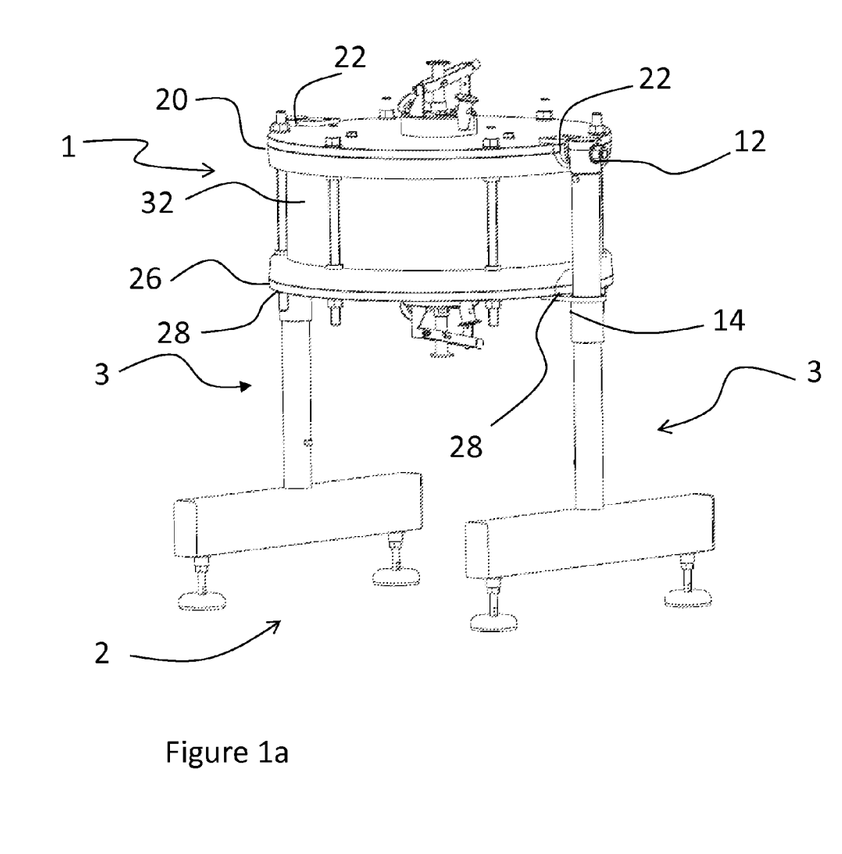
FIG. 1a shows one embodiment of a chromatography column and a stand according to the invention.
Figure 1B:
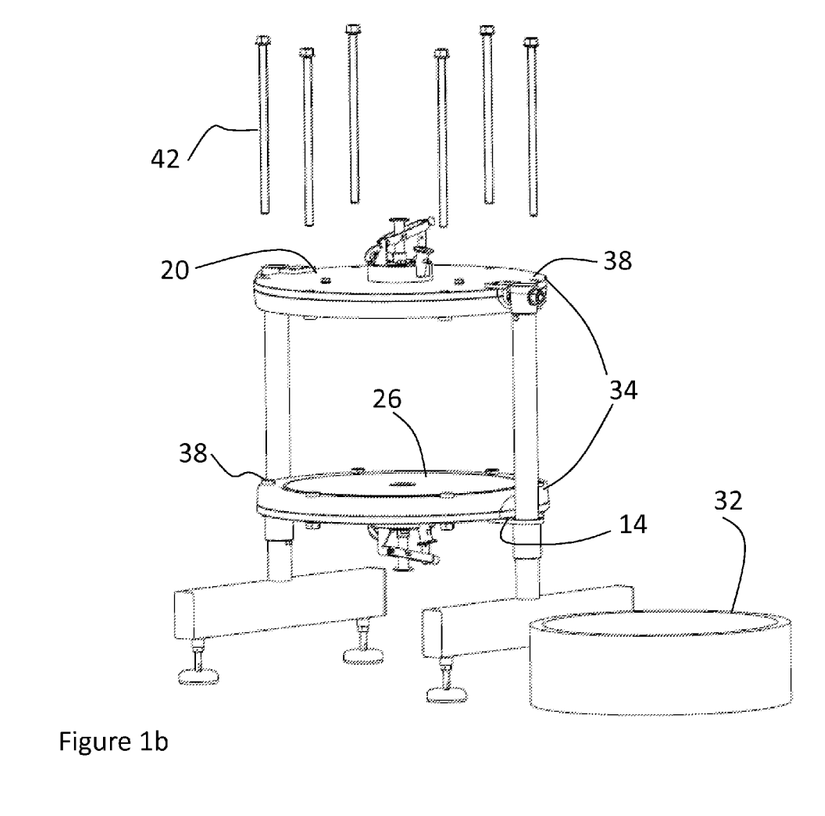
FIG. 1b shows the same chromatography column and stand as in FIG. 1a but column tube removed.

FIGS. 1a-1d show one embodiment of a chromatography column 1 and a stand 2 according to the invention. FIG. 1a shows the chromatography column 1 in an assembled position provided on the stand 2. FIG. 1b shows the same chromatography column as in FIG. 1a but disassembled. In this embodiment the stand 2 comprises two identical legs 3, also shown in FIG. 2. The legs 3 comprise one vertically oriented rod 4, which in its lower end 6 is fastened to the middle part of a horizontally oriented rod 8. The horizontally oriented rod 8 is adapted to rest on the ground via two feet 10 positioned one in each end of the horizontally oriented rod 8. Furthermore the vertically oriented rod 4 comprises a rotatable upper fastening means 12 and a lower fastening means 14 positioned below the upper fastening means 12, i.e. closer to the lower end 6 of the vertically oriented rod 4. The lower fastening means 14 can be adjusted vertically along the vertically oriented rod 4.

Now referring to FIGS. 1a-1d a top end cell 20 which is circular in shape comprises on its outer rim two diametrically opposed upper stand engaging means 22. The upper stand engaging means 22 are adapted to be engaged with the rotatable upper fastening means 12 on the stand. The top end cell 20 comprises typically a sample inlet/outlet, a distribution system, a filter, a net, O-rings and seals (not shown). A bottom end cell 26 also circular in shape comprises typically also inlet/outlet, distribution system, filter, net, O-rings and seals. It comprises also on its outer rim two diametrically opposed lower stand engaging means 28. The lower stand engaging means 28 are adapted to be engaged with the lower fastening means 14 on the stand.

The chromatography column also comprises a column tube 32 which during chromatography is positioned in between the top end cell 20 and the bottom end cell 26. The top end cell 20, the column tube 32 and the bottom end cell 26 thereby defines a volume where chromatography medium should be provided. The diameter of the column tube 32 is in this embodiment smaller than the outer diameter of the top end cell 20 and the bottom end cell 26. An outer rim 34 of both the top end cell 20 and the bottom end cell 26 comprise a number of holes 38 adapted to receive there through tie bars 42. The number of holes and tie bars can of course be varied. In FIG. 1b six tie bars and holes are shown but it could be any number. One tie bar 42 is adapted to penetrate one hole each in the top end cell 20 and the bottom end cell 26 when the column tube 32 is positioned there between. The tie bar 42 is then secured by fasteners to both the top end cell and the bottom end cell. Hereby the column tube 32 is secured steadily in between the top end cell and bottom end cell. Fluid tightening means such as O-rings can be provided for prevention of leakage.

Figure 1C:
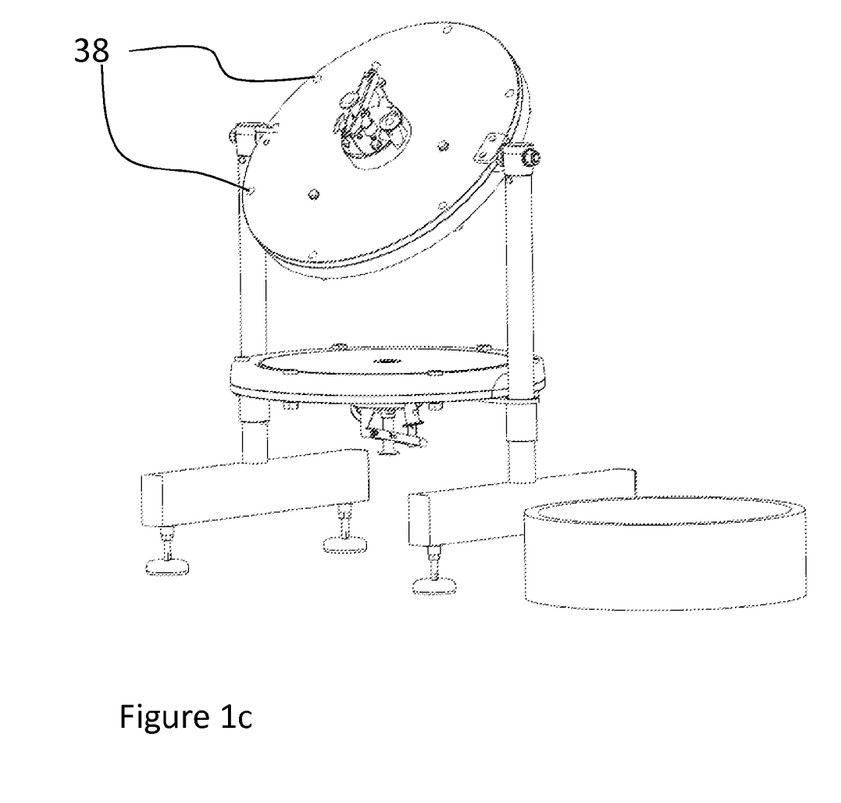
FIGS. 1c and 1d show the same chromatography column and stand as in FIG. 1a when the top end cell is rotated (1c) and has been rotated 180 degrees (1d).
Figure 1D:
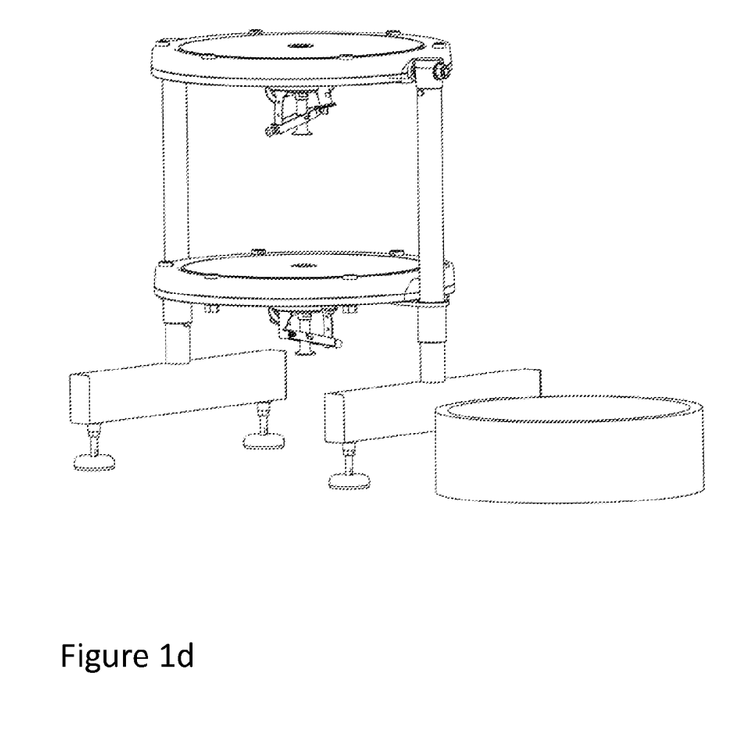

In FIG. 1b the chromatography column and the stand of FIG. 1a is shown where the bottom end cell 26 has been lowered, the tie bars 42 has been removed and the column tube 32 has been removed. The lower fastening means 14 of the stand 2 are as described above possible to adjust vertically along the legs 3 of the stand 2. FIG. 1*c* shows the same disassembled chromatography column as in FIG. 1*b* where the top end cell 20 is about to rotate. In FIG. 1*d* the top end cell 20 has been rotated 180 degrees. When the top end cell 20 has been flipped (rotated 180 degrees around a horizontal axis) maintenance is provided to the top end cell 20. The maintenance could be to exchange or clean parts such as filter, net, distribution system and seals. This is more easily done when the top end cell 20 has been rotated in situ according to the invention. The maintenance work is also safer for the personal when the gravitational force is used to keep parts together.

Figure 2:
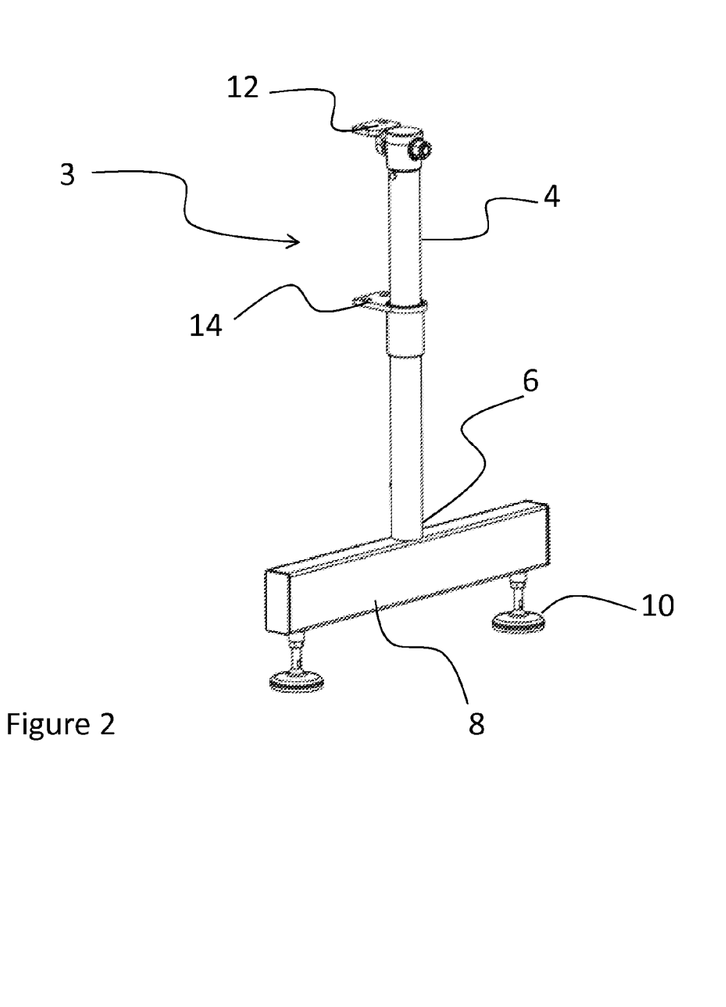
FIG. 2 shows one of the legs of the stand according to one embodiment of the invention.

FIGS. 3*a*, 3*b*, 3*c* and 3*d* show schematically the chromatography column 1 shown in FIGS. 1 and 2 in different positions during the maintenance procedure. The maintenance procedure is described below with reference to FIGS. 3*a*, 3*b*, 3*c* and 3*d*.

Figures 3A, 3C:
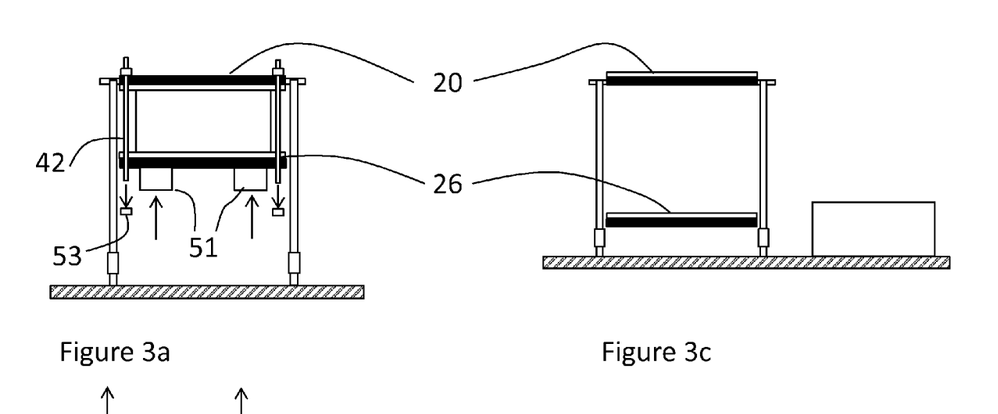
FIGS. 3a-3d show schematically a chromatography column according to one embodiment of the invention in different positions during the maintenance procedure.

In FIG. 3*a* it is shown how a lifting device 51 such as a scissor jack or a pallet lifter is provided underneath and against the bottom end cell 26 of the chromatography column. It is also shown how the tie bars 42 are released from the bottom end cell 26. The tie bars 42 are for example secured to the bottom end cell by nuts 53 as described above in relation to FIG. 2. By removing these nuts 53 the tie bars 42 can be released from the bottom end cell 26.

Figure 3B:
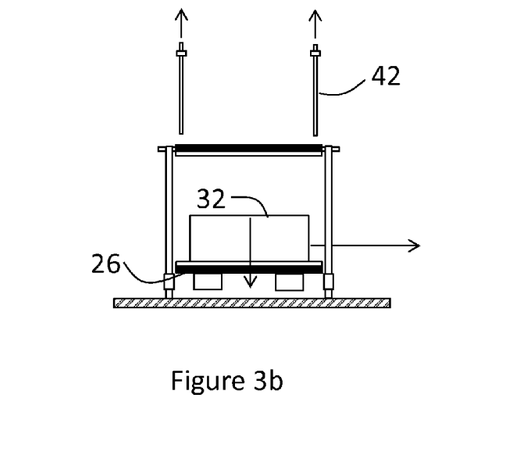

In FIG. 3*b* it is shown how the bottom end cell 26 and column tube 32 are lowered by use of the lifting device. The tie bars 42 can also be removed completely. The column tube 32 is removed. Depending on how large the column tube is it can be removed by hand or by some kind of lifting device.

In FIG. 3*c* it is shown how the top end cell 20 is flipped, i.e. rotation in situ of the top end cell 20 180 degrees around a horizontal axis. This is possible because the upper fastening means 12 on the stand are rotatable. This could possibly involve the removal of a locking device for allowing the top end cell 20 to rotate. A locking device could also be provided for locking the top end cell 20 in the rotated position.

Now maintenance can be conducted to the top end cell 20. This can involve disassembly of the parts constituting the top end cell, such as distribution system, nets, filter, O-rings and seals. Parts can be cleaned and parts can be exchanged. The rotated position of the top end cell 20 makes it easier and more convenient to disassemble the parts because the gravity force helps keeping the parts together even when the fasteners keeping them together have been removed. Hereby maintenance is facilitated and security improved.

Figure 3D:
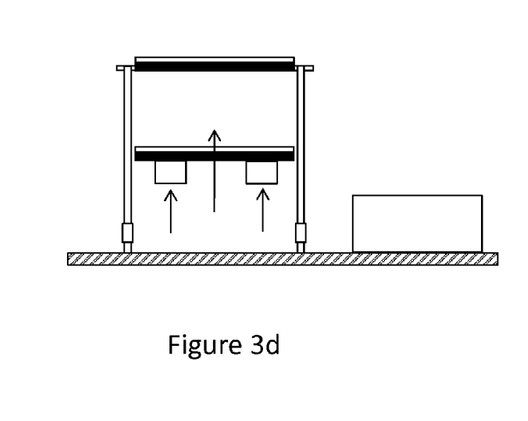

In one embodiment of the invention the bottom end cell 26 is raised by use of the lifting device. This would make it easier to reach and release the fasteners keeping the parts of the bottom end cell together. Possibly the bottom end cell could also be flipped as the top end cell in order to make it even easier to disassemble the bottom end cell. In that case the lower fastening means 14 of the stand also need to be rotatable. The raising of the bottom end cell 26 is shown in FIG. 3*d*.

Now maintenance is conducted also on the bottom end cell 26. This could involve disassembly of the parts constituting the bottom end cell, cleaning of the parts and/or exchange of parts.

Figure 4A:
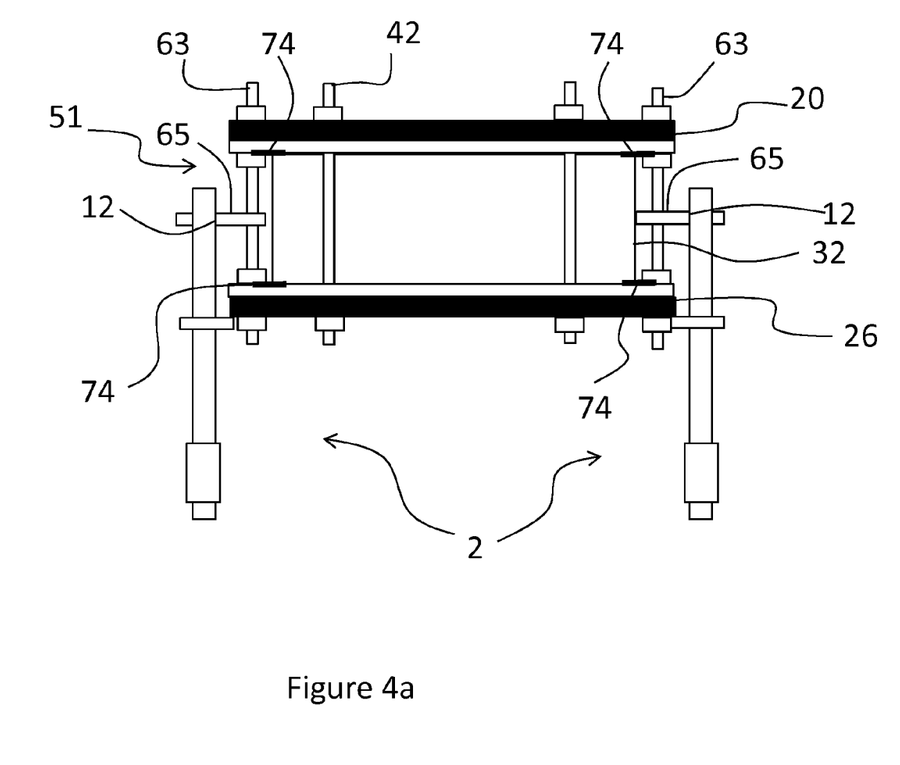
FIGS. 4a-4e show schematically a chromatography column according to another embodiment of the invention in different positions during the maintenance procedure.

In FIG. 4*a*-4*e* another embodiment of the invention is shown schematically in different positions during the maintenance procedure. The same reference numbers are given to the same parts as described in relation to FIGS. 1-4. FIG. 4*a* shows a chromatography column 51 provided on a stand 2. The stand 2 can be the same stand as described in FIG. 2. The chromatography column 51 comprises a top end cell 20, a bottom end cell 26 and secured there between a column tube 32. The column tube 32 is secured between the top end cell 20 and the bottom end cell 26 by tie bars 42 passing through holes in the outer rim of both the top end cell and the bottom end cell as described above in relation to FIG. 1. In this embodiment two diametrically opposed additional tie bars 63 are provided with upper stand engaging means 65 positioned in the middle of these tie bars 63. The upper stand engaging means 65 are adapted to engage into rotatable upper fastening means 12 of the stand 2. Hereby the swiveling point is in the center of gravity of the column. The bottom end cell 26 is possibly further secured to the stand 2 by lower stand engaging means 28 adapted to engage into lower fastening means 14 of the stand. The lower fastening means 14 are as also described in relation to FIG. 2 movable vertical along the stand. Furthermore column securing means 74 are provided on the two additional tie bars 63. The column securing means 74 are keeping the column secured to the opposed end cell even if the closest end cell is removed.

Figure 4B:
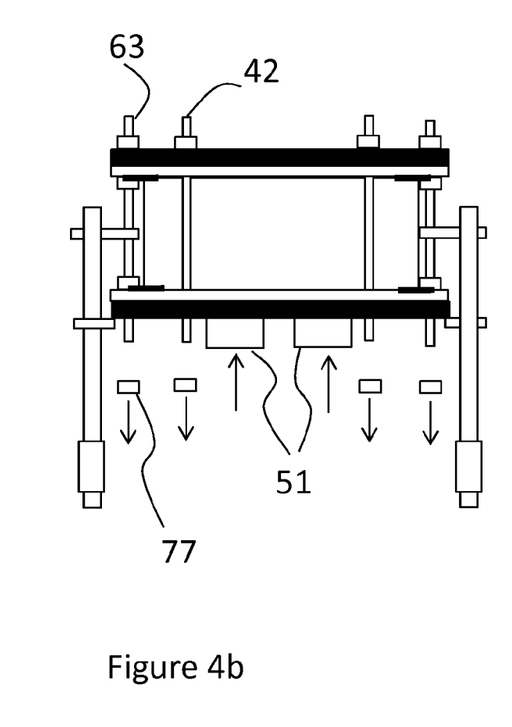

In FIG. 4*b* a lifting device for example a pallet lifter 51 is provided underneath the column. Lower fasteners 77 provided to the tie bars 42 and the additional tie bars 63 for keeping the bottom end cell 26 secured to the column tube 32 are removed.

Figure 4C:
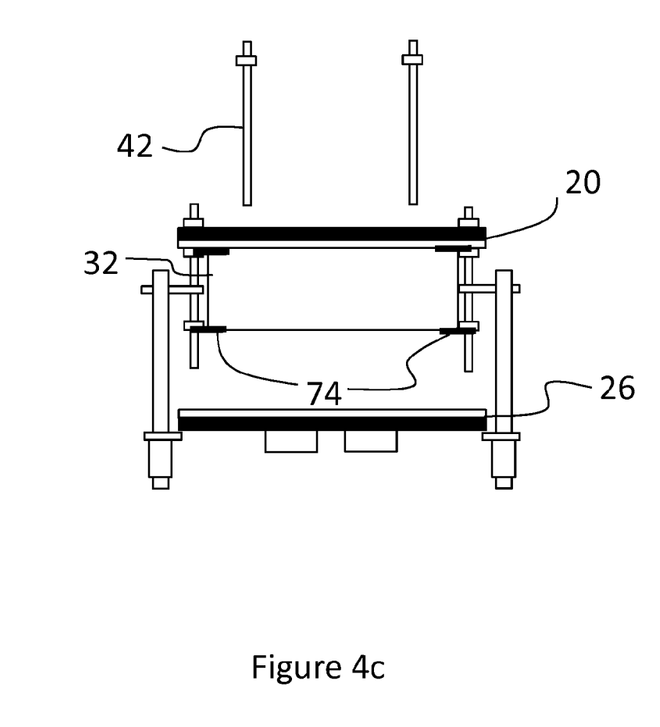

In FIG. 4*c* the tie bars 42 are removed and the bottom end cell 26 is lowered by use of the pallet lifter 51. Maintenance can now be performed on the bottom end cell 26. The column securing means 74 are now keeping the column tube 32 against the top end cell 20.

Figure 4D:
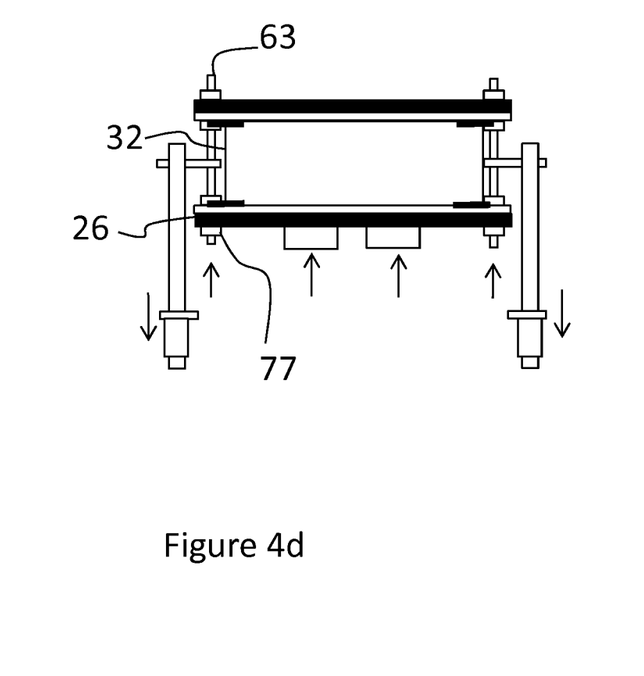

In FIG. 4*d* the bottom end cell 26 is raised up against the column tube 32 by use of the pallet lifter 51. Then fasteners 77 are mounted on the additional tie bars 63 hereby keeping the bottom end cell 26 together with the column tube 32.

Figure 4E:
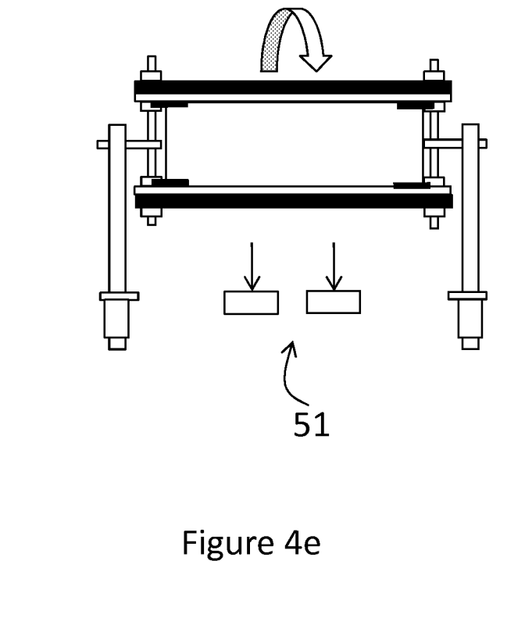

In FIG. 4*e* the pallet lifter 51 is removed and the column is rotated in situ 180 degrees around a horizontal axis. After the rotation the top end cell 20 is in the position where the bottom end cell 26 was from the beginning. Now the top end cell 20 can be lowered and maintenance can be provided to the top end cell in the same way as described for the bottom end cell in relation to the FIGS. 4*b*-4*d*.

Hereby, like in the embodiment described in relation to FIGS. 1-3, the rotated position of the top end cell 20 makes it easier and more convenient to disassemble the parts because the gravity force helps keeping the parts together even when the fasteners keeping them together have been removed. Hereby maintenance is facilitated and security improved.

One advantage with the method described in relation to FIGS. 4*a*-4*e* where the whole column is rotated instead of only the top end cell is that the column tube needs not to be lifted out. This could be especially advantageous for larger columns. With this described method the maintenance procedure will also be exactly the same for both top and bottom end cell.

Figure 5A:
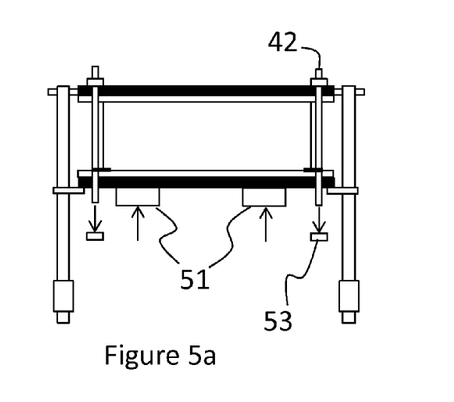
FIGS. 5a-5d show schematically a chromatography column according to another embodiment of the invention in different positions during the maintenance procedure.

In FIGS. 5*a*-5*d* another embodiment of the invention is shown schematically in different positions during the maintenance procedure. Most of the parts are the same as in FIGS. 1-3 and are also given the same reference numbers as in FIGS. 1-3. These parts will not be further described here. In FIG. 5*a* a lifting device 51 is provided underneath the column and the lower fasteners 53 are released from the tie bars 42.

Figure 5B:
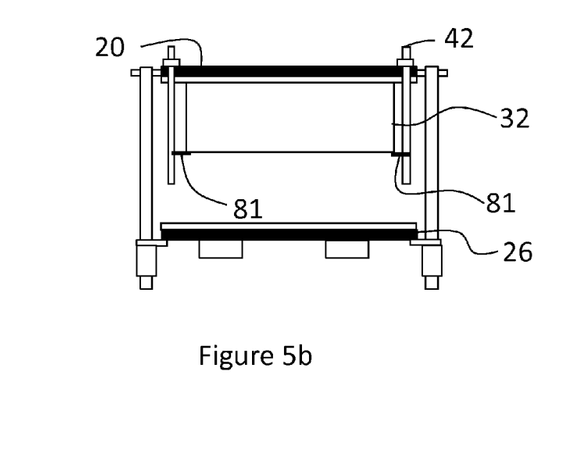

In FIG. 5*b* it can be seen that column securing means 81 are provided to at least some of the tie bars 42 in this embodiment for keeping the column tube 32 in place against the top end cell 20 when the bottom end cell 26 is lowered for maintenance.

Figure 5C:
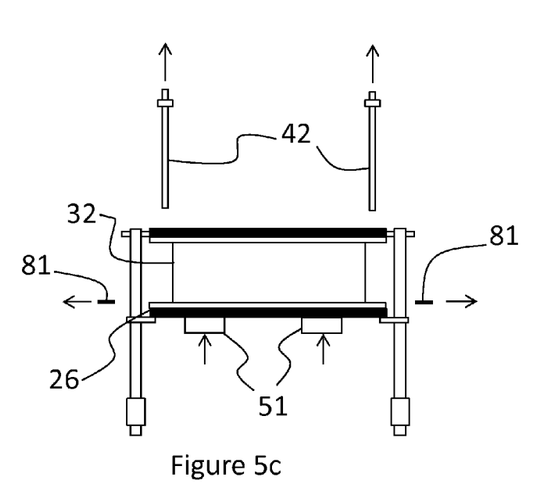

In FIG. 5*c* it is shown that after maintenance of the bottom end cell 26 the bottom end cell 26 is raised against the column tube 32 with the lifting device 51. Then the column securing means 81 are removed and the tie bars 42 are also removed.

Figure 5D:
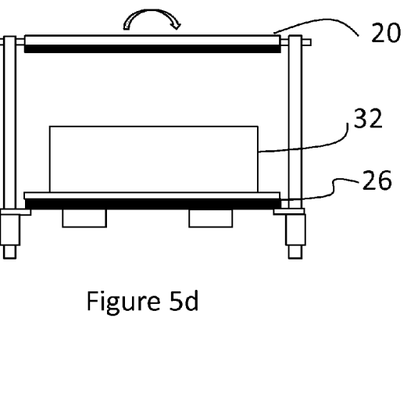

In FIG. 5*d* it is shown that the bottom end cell 26 is lowered together with the column tube 32 and the top end cell 20 has been rotated in situ 180 degrees around a horizontal axis for maintenance.

The embodiment described in relation to FIGS. 5*a*-5*d* could be especially suitable when large column tubes are handled because there is no need to remove the column tube.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for conducting maintenance on a chromatography column (1; 51), said column comprising a column tube (32), a top end cell (20) and a bottom end cell (26), where during chromatography said column tube (32) is secured between said top end cell (20) and said bottom end cell (26), said method comprising the step of rotating, in situ, at least the top end cell (20) 180 degrees around a horizontal axis before maintenance is conducted to the top end cell (20).

2. The method for conducting maintenance on the chromatography column (1) of claim 1, wherein said top end cell (20) being secured to rotatable upper fastening means (12) on a stand (2), said method comprising the steps of:
   a) releasing the bottom end cell (26) and the column tube (32) from the top end cell (20);
   b) lowering the bottom end cell (26) and the column tube (32);
   c) rotating the top end cell (20) 180 degrees around a horizontal axis; and
   d) conducting maintenance to the top end cell (20).

3. The method of claim 2, further comprising the steps of:
   a) removing the column tube (32); and
   b) conducting maintenance to the bottom end cell (26).

4. The method of claim 3, further comprising raising the bottom end cell (26) before conducting maintenance to it.

5. The method of claim 3, further comprising rotating the bottom end cell (26) during the maintenance.

6. The method of claim 1, wherein said chromatography column (51) is secured to rotatable upper fastening means (12) on a stand (2), said method comprising the steps of:
   a) releasing the bottom end cell (26) from the top end cell (20) and the column tube (32);
   b) lowering the bottom end cell (26);
   c) conducting maintenance to the bottom end cell (26);
   d) raising the bottom end cell (26) and securing it to the column tube (32) and the top end cell (20);
   e) rotating the chromatography column (51) 180 degrees around a horizontal axis;
   f) releasing the top end cell (20) from the bottom end cell (26) and the column tube (32);
   g) lowering the top end cell (20); and
   h) conducting maintenance to the top end cell (20).

7. The method for conducting maintenance on the chromatography column (1) of claim 1, wherein said top end cell (20) being secured to rotatable upper fastening means (12) on a stand (2), said method comprising the steps of:
   a) releasing the bottom end cell (26) from the top end cell (20) and the column tube (32);
   b) lowering the bottom end cell (26);
   c) conducting maintenance to the bottom end cell (26);
   d) raising the bottom end cell (26) against the column tube (32);
   e) releasing the column tube (32) form the top end cell (20); lowering the bottom end cell (26) together with the column tube (32);
   g) rotating the top end cell (20) 180 degrees around a horizontal axis; and
   h) conducting maintenance to the top end cell (20).

* * * * *